United States Patent
Hensberger et al.

(10) Patent No.: US 9,263,212 B2
(45) Date of Patent: Feb. 16, 2016

(54) HIGH VOLTAGE GAS CIRCUIT BREAKER GAS DENSITY MONITORING SYSTEM

(71) Applicant: MITSUBISHI ELECTRIC POWER PRODUCTS, INC., Warrendale, PA (US)

(72) Inventors: Jeremy A. Hensberger, Gibsonia, PA (US); Kevin J. Goldstein, Allison Park, PA (US); Edward J. Besong, Evans City, PA (US)

(73) Assignee: MITSUBISHI ELECTRIC POWER PRODUCTS, INC., Warrendale, PA (US)

(*) Notice: Subject to any disclaimer, the term of this patent is extended or adjusted under 35 U.S.C. 154(b) by 52 days.

(21) Appl. No.: 14/178,007

(22) Filed: Feb. 11, 2014

(65) Prior Publication Data
US 2014/0224770 A1 Aug. 14, 2014

Related U.S. Application Data

(60) Provisional application No. 61/763,386, filed on Feb. 11, 2013.

(51) Int. Cl.
*H01H 33/56* (2006.01)
*G01N 9/36* (2006.01)

(52) U.S. Cl.
CPC .............. *H01H 33/563* (2013.01); *G01N 9/36* (2013.01)

(58) Field of Classification Search
CPC ................. H01H 2033/906; H01H 2033/908; H01H 2223/002; H01H 33/22; H01H 33/563
See application file for complete search history.

(56) References Cited

U.S. PATENT DOCUMENTS

| | | | | |
|---|---|---|---|---|
| 4,027,125 A | * | 5/1977 | Peek | H01H 3/30 200/308 |
| 5,502,290 A | * | 3/1996 | Koyanagi | H01H 33/34 200/82 B |
| 6,263,914 B1 | * | 7/2001 | Meyer | G01N 9/266 137/377 |
| 6,651,483 B1 | * | 11/2003 | Meyer et al. | 73/23.28 |
| 8,822,870 B2 | * | 9/2014 | Mantilla | H01B 3/56 218/118 |
| 2007/0027640 A1 | * | 2/2007 | Rhodes | G01M 3/3236 702/51 |
| 2013/0277334 A1 | * | 10/2013 | Mantilla | H01B 3/56 218/85 |
| 2015/0043121 A1 | * | 2/2015 | Urai | H01H 33/38 361/115 |

* cited by examiner

*Primary Examiner* — Truc Nguyen
(74) *Attorney, Agent, or Firm* — One LLP

(57) ABSTRACT

A gas density monitoring system for high voltage gas circuit breakers. The gas density monitoring system comprising a gas density device mounted directly on a circuit breaker tank end cover. When the gas density device is fully secured to the tank end cover, the gas density device works in conjunction with a self-sealing valve body to provide a self-sealing, direct pathway between the pressurized tank and a sensing element of the gas density device. This pathway permits the gas density device to sense the circuit breaker tank pressure via an angled port through the tank end cover that limits pressure transients that may result from the normal operation of the circuit breaker. The gas density device contact settings may be verified without removal of the density device from the gas circuit breaker or venting the enclosed gas inside the gas circuit breaker to the atmosphere.

14 Claims, 8 Drawing Sheets

HIGH VOLTAGE GAS CIRCUIT BREAKER GAS DENSITY MONITORING SYSTEM

CROSS-REFERENCE TO RELATED APPLICATIONS

This application claims the benefit of and priority to U.S. Provisional Application No. 61/763,386, filed Feb. 11, 2013, and titled "High Voltage Gas Circuit Breaker Gas Density Monitoring System," which is incorporated by reference herein in its entirety for all purposes.

FIELD

The embodiments described herein relate generally to high voltage gas circuit breakers and, more particularly, to systems and methods that facilitate gas density monitoring.

BACKGROUND INFORMATION

High voltage circuit breakers are used in the transmission and distribution of three phase electrical energy. The circuit breakers operate to physically separate current-carrying contacts in each of the three phases by opening the circuit to prevent the continued flow of current in response to a sensor or protective relay fault or other system disturbance detection on the protected circuit. The circuit breakers include interrupters, which function to open and close current carrying contacts, interrupter operating mechanisms and linkages, arcing control mechanisms and interrupting media, one or more tanks for housing the interrupters, and bushings, which carry the high voltage electrical energy from the protected circuit into and out of the tank(s) (in a dead tank breaker).

The tanks in which the circuit breakers are housed are typically filled with an inert gas, such as, e.g., SF6, which acts as an insulator to control arcing. An electrical arc, which is the result of a circuit breaker opening or closing, can develop across the switch contacts especially the closer the contacts are to closure. The inert gas is preferably maintained at a predetermined density to ensure that the inert gas insulates as designed. Due to possible leaks or system malfunctions, the density of the inert gas must be constantly monitored.

In conventional gas monitoring systems, gas from each of the tanks in a multi-tank circuit breaker system, is typically fed back to a single density monitoring device. If the density falls to an insufficient level, this design makes it difficult to determine which tank is actually experiencing the leak. In addition, the intricate piping system typically needed creates more places for leaks to occur.

In other gas monitoring systems, a gas monitoring device is installed in the vessel wall of each of the tanks. Although individual tank monitoring is enabled, such systems tend to require temperature compensation systems or complex mounting arrangements due to space constraints and suffer from reduced accuracy.

Thus, it is desirable to provide improved systems and methods that facilitate gas density monitoring.

SUMMARY

The embodiments provided herein are directed to systems and methods that facilitate gas density monitoring in high voltage circuit breakers that utilize an inert gas, such as, e.g., SF6, as an insulator. More particularly the embodiments provided herein comprise a gas density device mounted directly on a tank end cover of a high voltage circuit breaker tank. The gas density device is coupled to the tank end cover via a mounting plate and hardware. When the gas density device is fully secured to the tank end cover, the gas density device works in conjunction with a self-sealing valve body to provide a direct pathway between the pressurized tank and a sensing element of the gas density device. Other shut off valves such as a bellows or sliding seal in a cylinder can be used to reduce the density (increase the volume) without moving the monitor. This pathway permits the gas density device to sense the circuit breaker tank pressure via an angled port through the tank end cover that limits pressure transients that may result from the normal operation of the circuit breaker. Depending on the specified design functionality of the gas density device, the gas pressure and temperature will be measured to determine the density of the gas in the pressurized tank.

The gas density device contact settings may be verified without removal of the density device from the gas circuit breaker or venting the enclosed gas inside the gas circuit breaker to the atmosphere Other systems, methods, features and advantages of the example embodiments will be or will become apparent to one with skill in the art upon examination of the following figures and detailed description.

BRIEF DESCRIPTION OF THE FIGURES

The details of the example embodiments, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

It should be noted that elements of similar structures or functions are generally represented by like reference numerals for illustrative purpose throughout the figures. It should also be noted that the figures are only intended to facilitate the description of the preferred embodiments.

DETAILED DESCRIPTION

The embodiments provided herein are directed to systems and methods that facilitate gas density monitoring in high voltage circuit breakers that utilize an inert gas, such as, e.g., SF6, as an insulator. More particularly the embodiments provided herein comprise a gas density device mounted directly on a tank end cover of a high voltage circuit breaker tank. The gas density device is coupled to the tank end cover via a mounting plate and hardware. When the gas density device is fully secured to the tank end cover, the gas density device works in conjunction with a self-sealing valve body to provide a direct pathway between the pressurized tank and a sensing element of the gas density device. This pathway permits the gas density device to sense the circuit breaker tank pressure via an angled port through the tank end cover that limits pressure transients that may result from the normal operation of the circuit breaker. Depending on the specified design functionality of the gas density device, the gas pressure and temperature will be measured to determine the density of the gas in the pressurized tank. The gas density device will then determine the appropriate output response (no alarm, alarm, proportional analog signal, etc.) and provide an output signal to the main control housing.

The gas density device is capable of performing one or more of the following active functions:
 a. Signaling remote alarm contacts when gas density has reached discrete minimum values;
 b. Transmitting continuous analog signals to additional control and monitoring equipment for monitoring gas pressure, temperature and density; and
 c. Provide visual indication of the high voltage circuit breaker tank pressure via a dial indicating device.

Figure 1A:
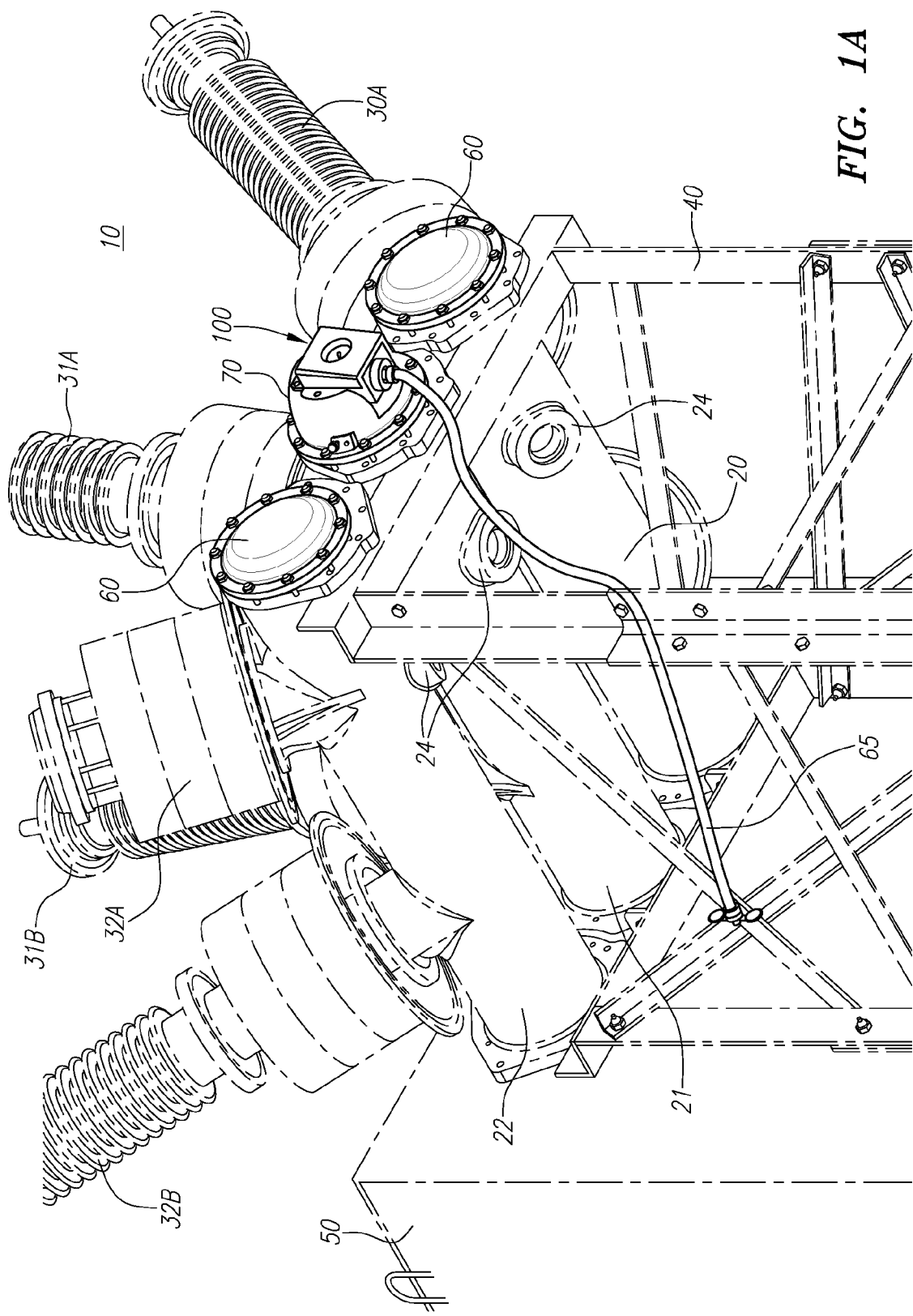
FIGS. 1A and 1B are perspective views of a multi-tank, high voltage circuit breaker with a tank end cover mounted gas density monitoring system.
Figure 1B:
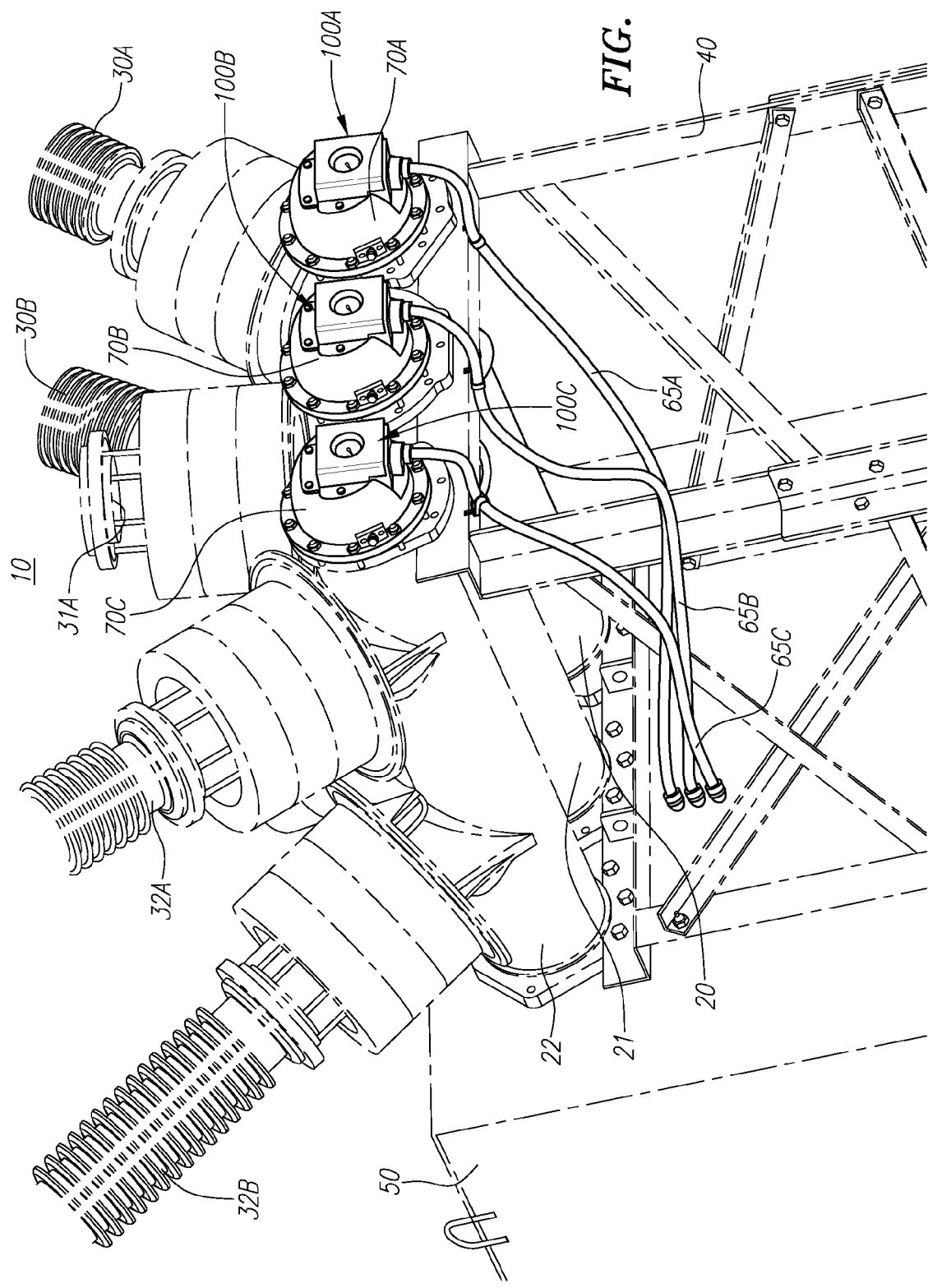

Turning in detail to the figures, FIGS. 1A and 1B depict multi-tank high voltage circuit breaker systems 10 comprising first, second and third circuit breaker tanks 20, 21 and 22 housing one or more mechanical interrupter devices. The tanks 20, 21 and 22 are mounted on a steel frame 40 and are in communication with control components within a main control housing 50 also mounted the frame 40. Individual pairs of bushings 30A and 30B, 31A and 31B and 32A and 32B, respectively, extend from the tanks 20, 21 and 22. Each tank 20, 21 and 22 includes a rupture disk 24 positioned opposite the bushings.

Figure 2:
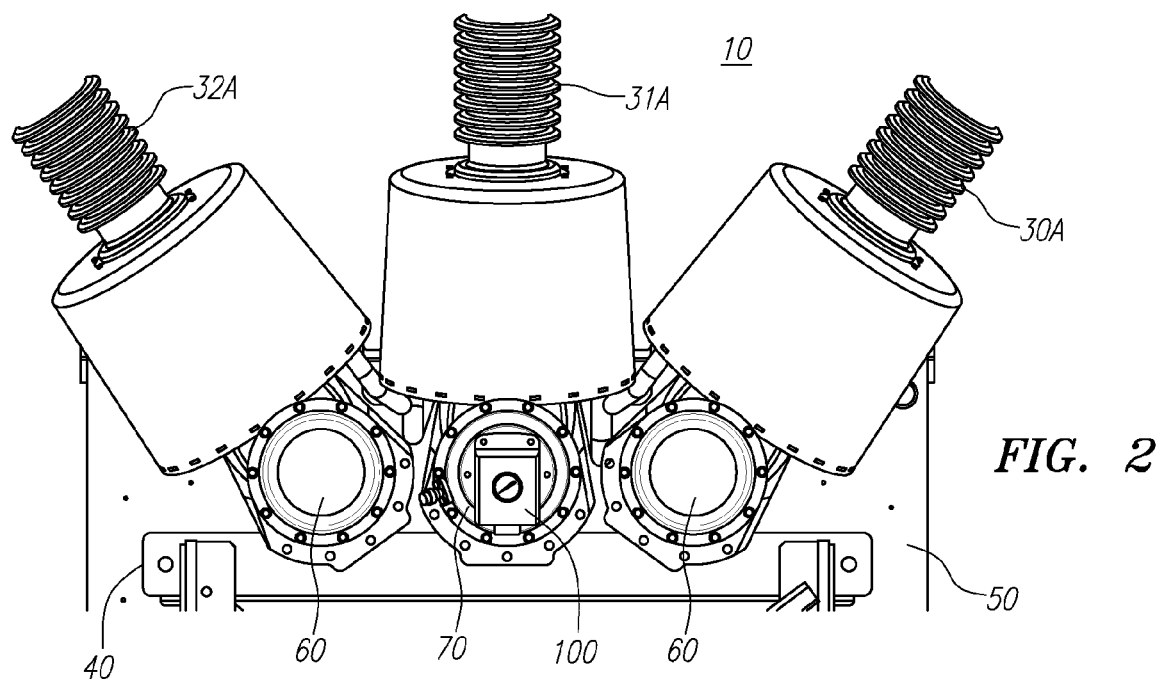
FIG. 2 is a partial end view of the multi-tank, high voltage circuit breaker shown in FIG. 1A.

Referring to FIGS. 1A and 2, the first and third tanks 20 and 22 are shown to include conventional tank end covers 60, while the second tank 21 is shown to include a monitoring tank end cover 70 configured to mount a gas density device 120 (see FIGS. 3 and 4) of a gas density device assembly 100 that is used to commonly monitor the density of the gas in the first, second and third tanks 20, 21 and 22. One of ordinary skill in the art would readily recognize that a variety of gas density devices can be mounted to the system and need not be limited to the gas density device 120 shown in FIGS. 3 and 4. As shown, an electrical conduit 65 extends from the gas density device of the gas density device assembly 100 back to the main control housing 50.

FIG. 1B provides an alternative embodiment where the density of the gas in the first, second and third tanks 20, 21 and 22 is monitored individually. More particularly, each of the first, second and third tanks 20, 21 and 22 include a monitoring tank end cover 70A, 70B and 70C configured to mount a gas density device 120 (see FIGS. 3 and 4) of gas density device assemblies 100A, 100B and 100C. As shown, individual electrical conduits 65A, 65B and 65C extend from the gas density device of each of the gas density device assemblies 100A, 100B and 100C back to the main control housing 50.

All electrical components (wire, connections, etc.) from the main control housing 50 to the gas density device 120 are enclosed in the main control cabinet 50, liquid-tight conduit 65, or the housing of the gas density device 120.

Figure 3:
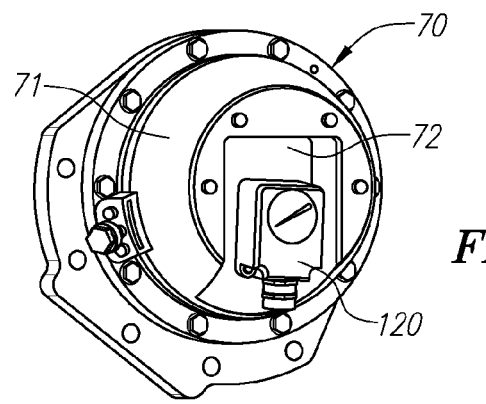
FIG. 3 is a perspective view of a tank end cover with a gas density device coupled thereto.
Figure 4:
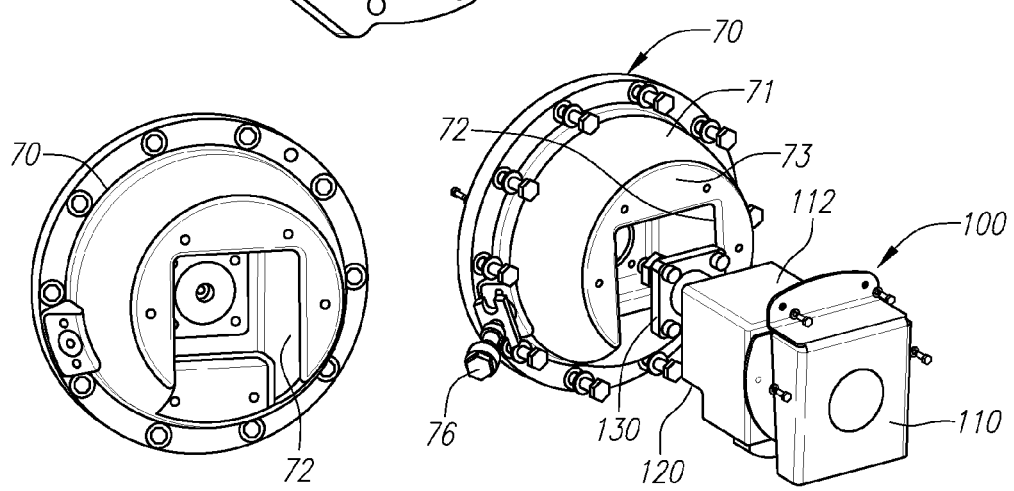
FIG. 4 is a multi-view perspective of the tank end cover and an exploded assembly of the gas density device assembly.

As shown in FIGS. 3 and 4, the gas density device 120 is mounted on the monitoring tank end cover 70 within a recess 72 formed in the body 71 of the end cover 70 using a mounting plate 130. The gas density device assembly 100 is shown to further include a thermal insulator cover 112 covering the gas density device 120 and a solar shield 110 covering the thermal insulator 112 and coupling to an end face 73 of the tank end cover 70.

The thermal insulation cover 112 is installed around the gas density device 120 to minimize ambient temperature effects and maintain the gas density device sensing element at a stable temperature referencing the gas temperature as effectively as possible. The solar shield 110 is installed on the tank end cover 70 over the thermal insulation cover 112 to minimize the effect of solar radiation on the gas density sensing element of the gas density device 120 and add a level of protection to the thermal insulation cover 112 against UV degradation.

Figure 5:
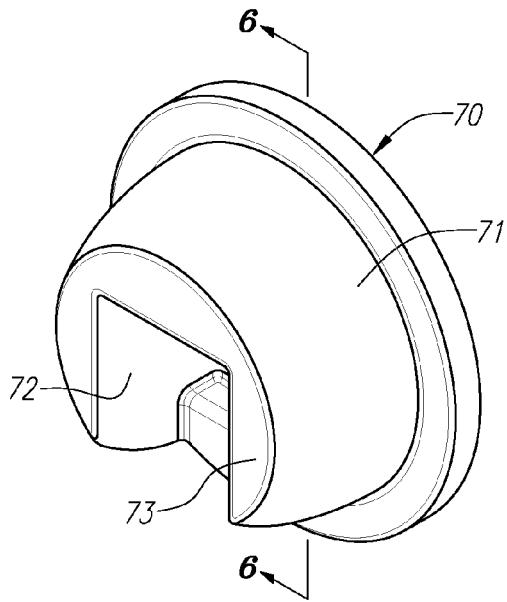
FIG. 5 is a perspective view of the tank end cover.
Figure 6:
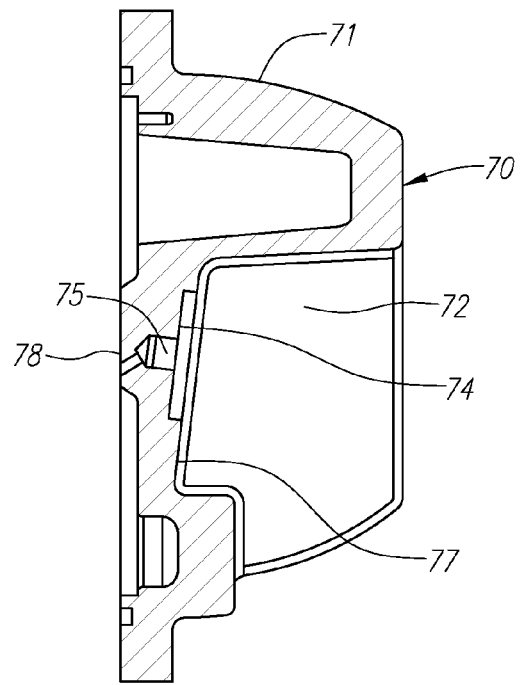
FIG. 6 is a cross-sectional view of the tank end cover taken along line 6-6 in FIG. 5.
Figure 7:
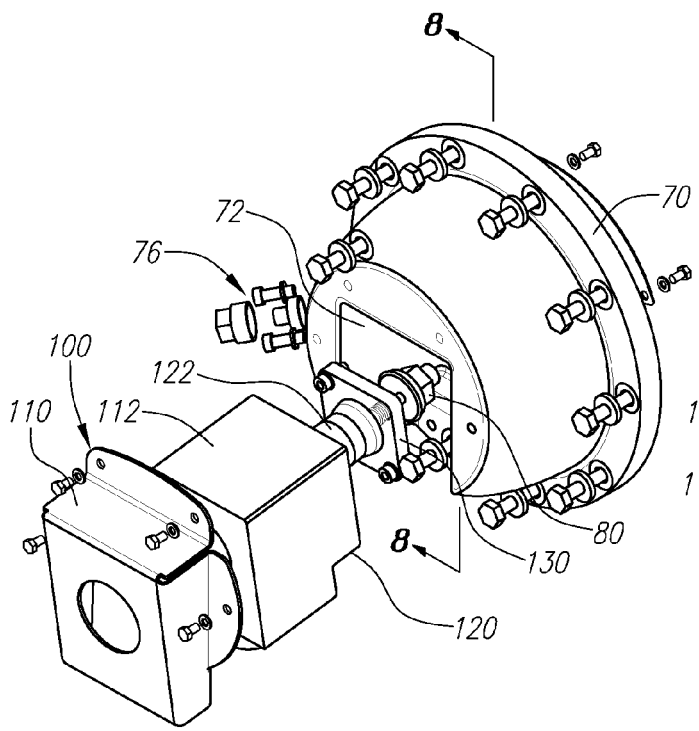
FIG. 7 is a perspective view of an exploded assembly of the end cover, self sealing valve, gas density device, thermal insulation and solar cover.

Referring to FIGS. 5 and 6, the body 71 of the monitoring tank end cover 70, which when viewed toward the end face 73 appears circular in shape, is shown to include a recess 72 for mounting the gas density device 120. A back wall 77 includes holes tapped therein used to couple the mounting plate 130 of the gas density device 120. A valve and connecting flange recess 74 is formed in the back wall 77. At about the horizontal and vertical centerlines of the tank end cover 70, a manifold 75 is formed as a hole tapped into the body 71 of the end cover 70 from the valve and connecting flange recess 74. An angled gas port 78 is open to the interior of the end cover 70 (and, thus, the circuit breaker tank) and extend through the body 71 and opens up into the manifold 75. When the end cover 70 is coupled to the end of a circuit breaker tank, the angled gas port 78 provides access to the interior of the tank. As noted above, the pathway provided by the manifold 75 and angled port 78 provides a direct pathway from the interior of the tank to the gas density device 120 that permits the gas density device 120 to sense the circuit breaker tank pressure via the angled port 78 which limits pressure transients that may result from the normal operation of the circuit breaker.

Figure 8:
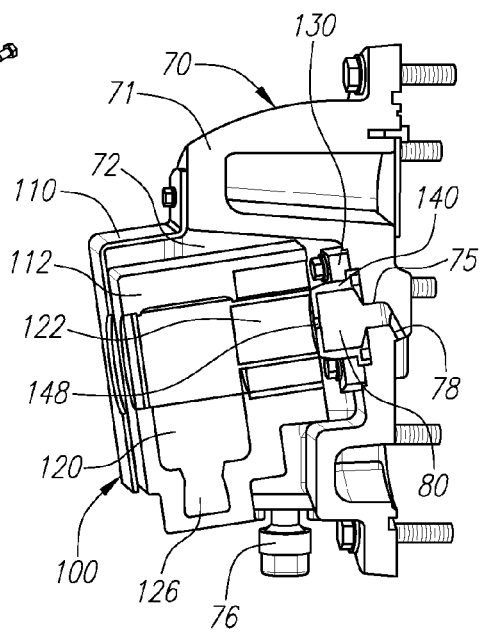
FIG. 8 is a cross-sectional view of the fully assembled components of the exploded assembly in FIG. 7 taken along line 8-8 in FIG. 7.
Figure 9:
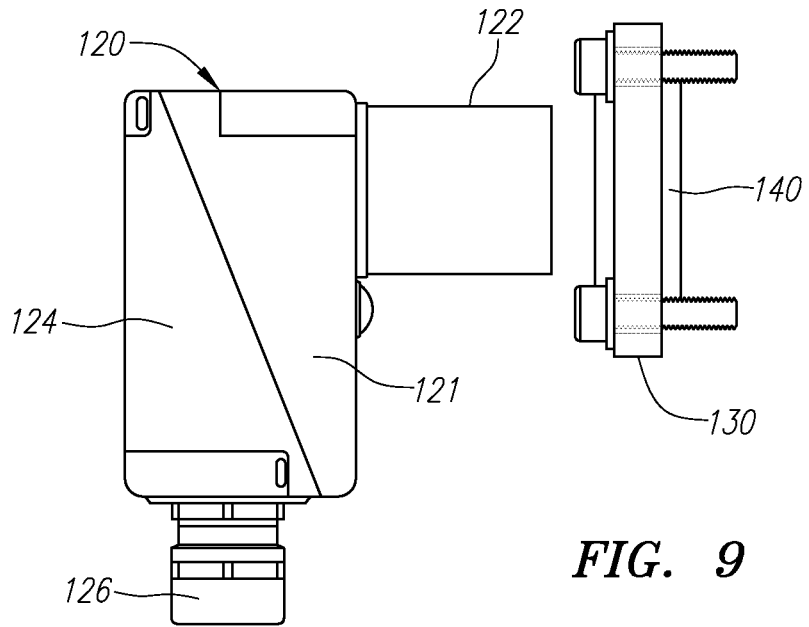
FIG. 9 is a side view of the gas density device.
Figure 10:
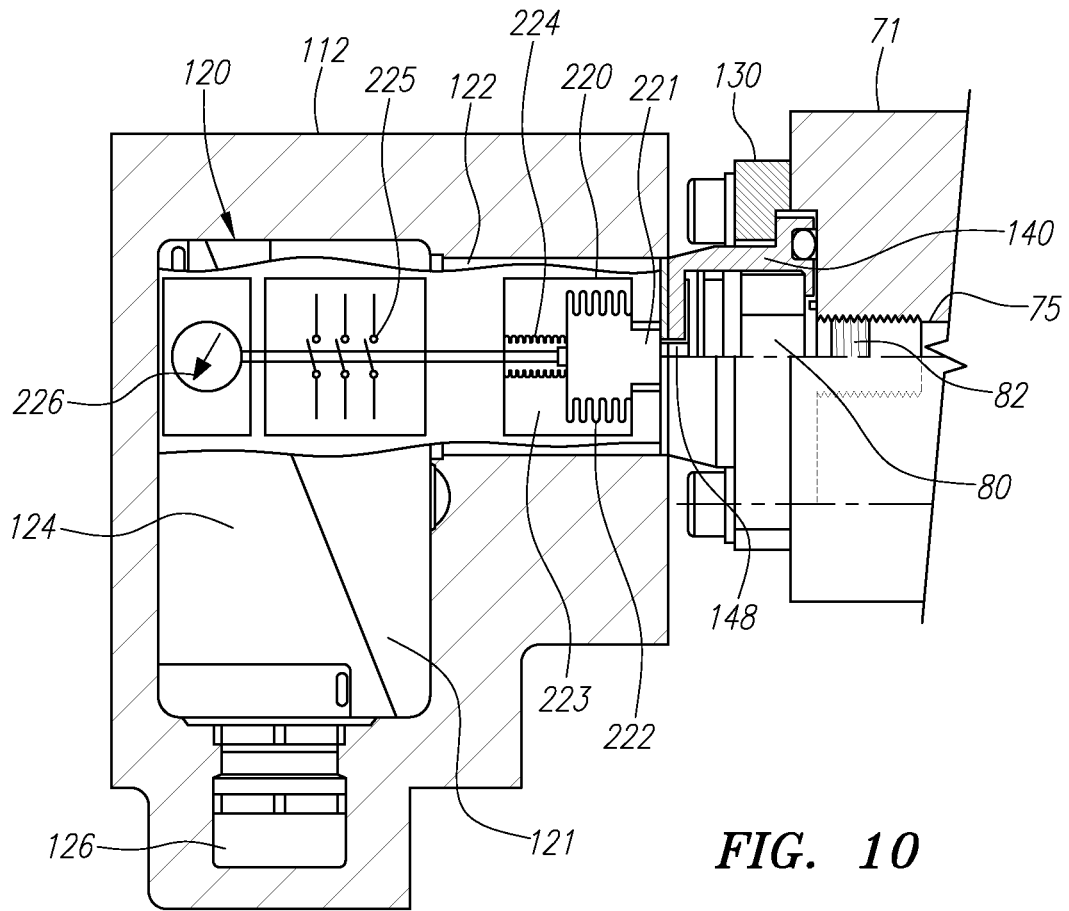
FIG. 10 is a partial detail cross-sectional view of the end cover, self sealing valve, gas density device and thermal insulation shown in FIG. 8.
Figure 11A:
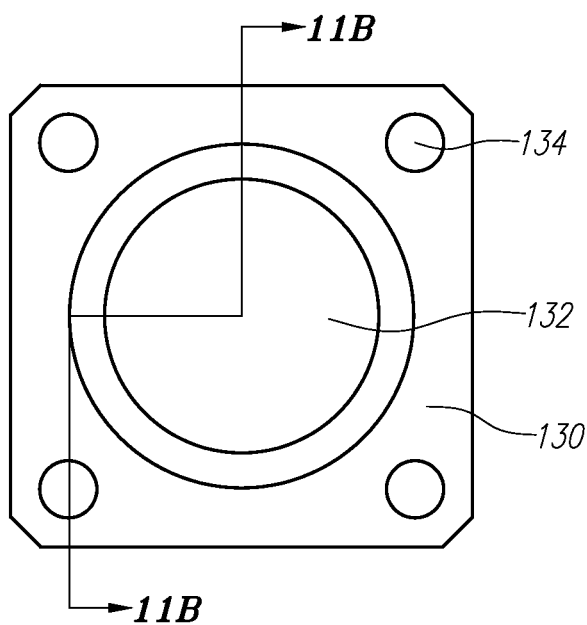
FIG. 11A is a plan view of a mounting plate of the gas density device.
Figure 11B:
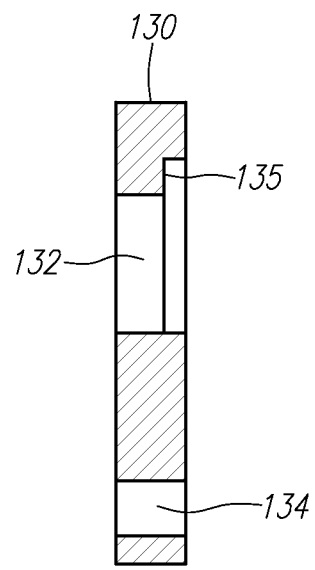
FIG. 11B is a cross-sectional view of the mounting plate taken along line 11B-11B in FIG. 11A.
Figure 12:
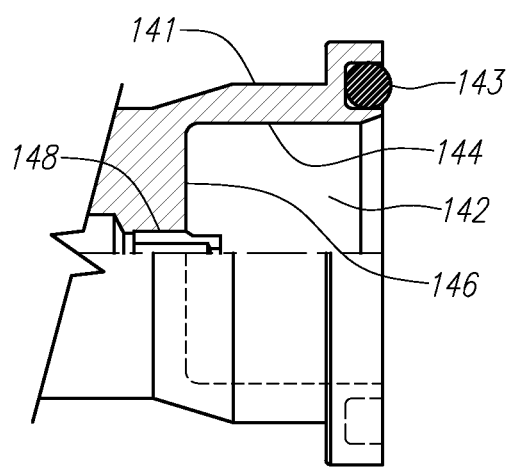
FIG. 12 is a partial detail cross-sectional view of a connecting flange of the gas density device shown in FIG. 10.
Figure 13:
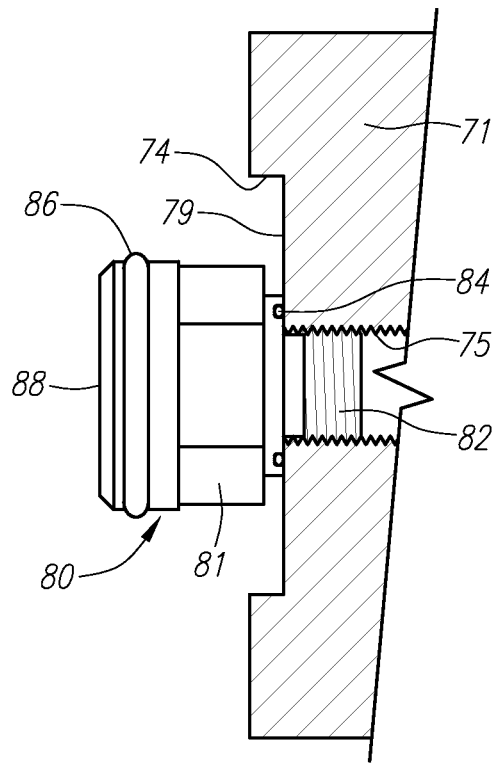
FIG. 13 is a partial detail cross-sectional view of the end cover and self sealing valve shown in FIG. 10.

Turning to FIGS. 7, 8, 9, 10, 11A, 11B, 12 and 13, the gas density device 120 is shown to work in conjunction with a self sealing valve 80. The self sealing valve 80, as shown in FIGS. 8, 10 and 13, includes a valve body 81 and a threaded valve stem 82 extending from the body 81. The threaded valve stem 82 screws into the tapped hole of the manifold 75 to securely mount the valve 80 on the tank end cover 70. An o-ring 84 is positioned between the valve body 81 and the face 79 of the valve and connecting flange recess 74 to provide a gas tight seal between the valve 80 to the end cover 70. At an end opposite the valve stem 82 is a circumferential o-ring 86 extending about the body 81 and a valve actuator 88 extending from the end of the body 81.

As shown in FIGS. 8-10, the gas density device 120 includes a gas sensing element 220 housed in gas sensing housing 122 extending from a micro-switch housing 121 opposite a cover 124. The gas sensing housing 122 is coupled to a connecting flange 140 at an end opposite the micro-switch housing 121. The flange 140, which can be coupled to or formed integrally with the gas sensing housing 122, includes a central hole 148 through its body 142 that is in communication with the interior of the gas sensing housing 122.

In the gas sensing element 220, the density of a sample gas is compared via a bellows system 221, 222 and 224 with the gas density of a reference gas in a reference gas chamber 223. If the density of the sample gas alters, the bellows system 221, 222 and 224 actuates one or more micro switches 225 in the micro-switch housing 121. In addition, an optional trend indicator, such as a pressure gauge 226, can be used to provide visual indication. Gas density controllers work without electrical energy and therefore need no electricity supply.

As shown in FIGS. 10 and 12, the flange 140 includes a cavity 142 that receives the self sealing valve 80 when the gas density device 120 is mounted on the end cover 70. The circumferential o-ring 86 provides a seal between the valve 80 and a side wall 144 of the cavity 142. A flange face o-ring 143 provides a seal between the flange 140 and the face 79 of the valve and connector flange recess 74. When mounted over the valve 80, a back wall 146 of the cavity 142 abuts the valve actuator 88 to actuate the valve 80 and enable gas to flow from the interior of the circuit breaker tank through the angled port 78, the valve 80, the central hole 148 and the gas conduit 122 to the gas sensing element 121; thus placing the gas density device 120 in communication with the interior of the circuit breaker tank over a self-sealing, direct pathway.

To mount the gas density device 120 to the end cover 70, the gas conduit 122 is passed through a hole 132 in the center of the mounting plate 130. An alignment recessed 135 formed in one of the faces of the mounting plate 130 receives the flange 140 and aligns the mounting plate 130 relative thereto. Mounting holes 134 about the periphery of the plate 130 are aligned with holes tapped in the back wall 77 of the recess 72 in the end cover 70 to mount the gas density device 120 to the end cover 70.

It is common during the commissioning and service of high voltage circuit breakers to check the gas density device contact set points. The set points of the gas density device 120 described herein can be checked in two distinct ways: A first method enables the contact set points of gas density device 120 to be checked without removal of the gas density device 120 and without the loss or venting of gas from the circuit breaker tank. A second method permits the contact set points of gas density device 120 to be checked by removal of the gas density device 120 from the tank end cover 70. A manifold test kit is then used to pressurize and test the gas density device 120, as well as attach auxiliary measurement devices if required.

In the event the gas density device 120 is required to be removed from the tank end cover 70, the use of the self-sealing valve 80 allows for removal of the gas density device 120 with the high voltage breaker tank pressurized. Use of the self sealing valve 80 eliminates the need to manually close valves or ports and passively prevents the loss of gas from the tank enclosure. Other shut off valves such as a bellows or sliding seal in a cylinder can be used to reduce the density (increase the volume) without moving the monitor.

Figure 14A:
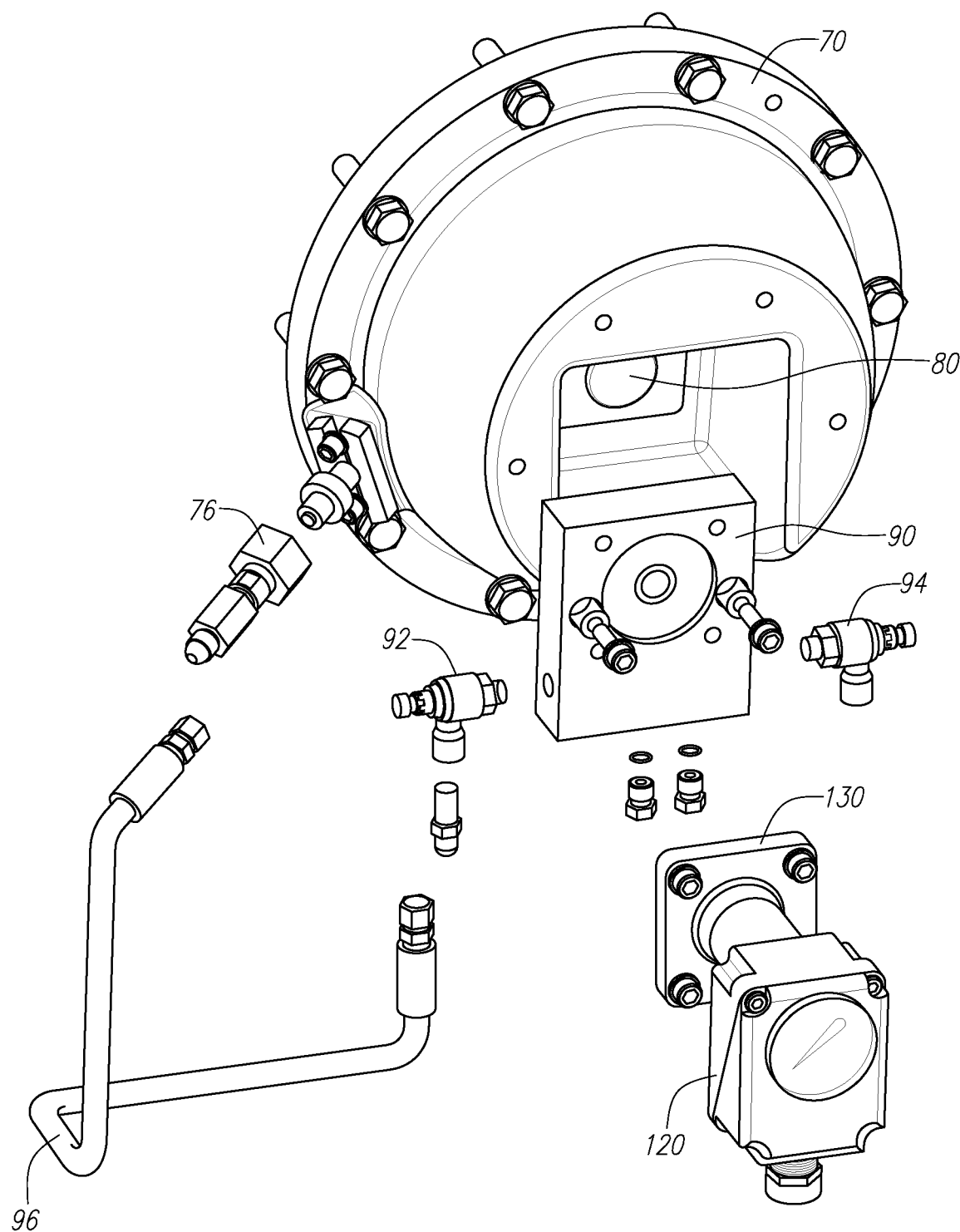
FIG. 14A is a perspective view of an exploded assembly of an end cover, a gas density device, and a test manifold kit.
Figure 14B:
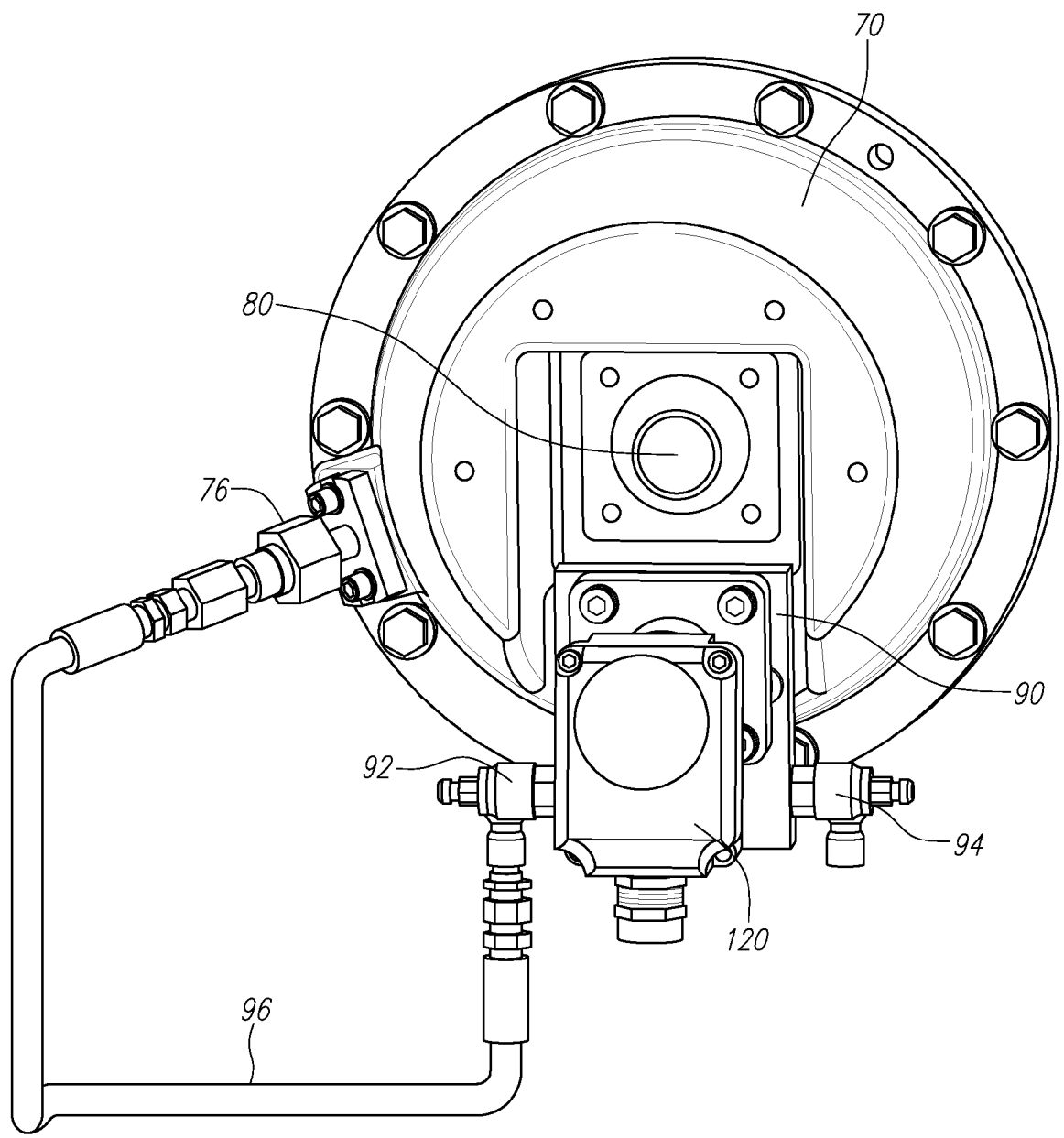
FIG. 14B is a perspective view of a fully assembled assembly of an end cover, a gas density device, and a test manifold kit.

Turning to FIGS. 14A and 14B, after the gas density device 120 is removed, a manifold 90 used for testing only is coupled to the end plate 70 at a position spaced away from the self sealing valve 80. The gas density device 120 is then coupled to the manifold 90. Pressurized air or N2 from a pressurized source can be supplied through a conduit 96 coupled to an inlet needle 92 at the inlet of the manifold 90 to test the contact set points of the gas density device 120. Alternatively, the conduit 96 can be coupled to the fill valve 76 on the fill port of the tank end cover 70, as shown in FIG. 14B, in order to use gas from the circuit breaker tank to test the contact set points of the gas density device 120. An outlet needle valve 94 is coupled to the outlet of the manifold 90 to exhaust gas from the manifold 90 and gas density device 120. The contact set points are tested in two directions, both rising pressure and falling pressure.

The embodiments provided herein permit the density of the gas in high voltage circuit breakers to be monitored continuously via the gas density device 120 mounted directly on the tank end cover 70 of the high voltage circuit breaker. The configuration of the gas density device 120 mounted directly on the end cover 70 of the high voltage circuit breaker tank eliminates the need to use auxiliary reference temperature sensors (capillary tubes, RTDs, etc.) and maintains a high level of accuracy with an intrinsic device. The placement of the gas density device 120 on the tank end cover optimizes the location at which the gas temperature can be sensed from an intrinsic temperature compensating element. Use of the tank centerline gas temperature as a reference temperature for the gas density device 120 can average the effects of the ambient environment and breaker operating conditions to form a highly accurate input to the gas density device 120.

The embodiments described herein advantageously provide:

i. A compact gas monitoring system that includes a self-sealing valve body 80, a gas density device 120, thermal insulation 112 and solar shielding 110;

ii. Provisions for testing of the contact set points and gas fill ports;

iii. Provisions for preventing transient pressure responses from impacting the gas density device 120 and providing a stable reference pressure;

iv. Angled indicator for easy recording of the gas pressure of an installed breaker by field personnel;

v. Protection of the gas density device 120 from external damage by encapsulating the device 120 within the cover body 110; and vi. Prevention of the loss of SF6 gas during the testing of the set points.

With the gas density device 120 mounted on the tank end cover 70, field retrofit (or "upgrade") is achievable by removing a tank end cover having a conventional design and replacing it with a cover equipped with the gas density monitoring system including a self sealing valve 80 and a gas density device 120. Additional electrical connections to the main control cabinet would be required, depending on the gas density device 120 output specifications. Any existing conventional gas density devices can be removed and the associated gas ports capped.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A gas circuit breaker comprising
a plurality of tanks, wherein individual ones of the plurality of tanks house an interrupter,
individual pairs of bushings coupled to individual ones of the plurality of tanks, and
one or more gas density devices, wherein individual ones of the one or more gas density devices are coupled to an end cover of individual ones of the plurality of tanks and in fluid communication over a self sealing pathway with an interior of the individual one of the plurality of tanks to which the end cover is coupled, wherein the self sealing pathway includes a self sealing valve mounted in the end cover and a gas port formed in the end cover at an angle to a longitudinal axis of the individual one of the plurality of tanks and open to the interior of the individual one of the plurality of tanks,
wherein the one or more gas density devices comprise
a gas sensing element,
a gas conduit extending from the gas sensing element, and
a connecting flange coupled to the gas conduit, wherein when the gas density device is coupled to the end cover the connecting flange operably couples to and actuates the self sealing valve.

2. The circuit breaker of claim 1 wherein the gas density device further comprises a mounting plate positionable over the gas conduit and operably coupled to the connecting flange when coupled to the end cover.

3. The circuit breaker of claim 1 wherein the gas density device includes one of a gas sensing element cover or a pressure gauge coupled to the gas sensing element.

4. The circuit breaker of claim 1 further comprising a thermal insulating cover surrounding the gas density device and a solar cover positionable over the thermal insulating cover and mountable to the end cover.

5. A gas circuit breaker tank comprising
a pressure vessel, the pressure vessel configured to house an interrupter device,
an end cap coupled to the pressure vessel, and
a gas density device coupled to the end cover of the pressure vessel and in fluid communication over a self sealing pathway with an interior of the pressure vessel, wherein the self sealing pathway includes a self sealing valve mounted in the end cover,
wherein the gas density device comprises
a gas sensing element,
a gas conduit extending from the gas sensing element, and
a connecting flange coupled to the gas conduit, wherein when the gas density device is coupled to the end cover the connecting flange operably couples to and actuates the self sealing valve.

6. The circuit breaker of claim 5 wherein the self sealing pathway further comprises a gas port formed in the end cover at an angle to a longitudinal axis of the pressure vessel and open to the interior of the pressure vessel.

7. The circuit breaker of claim 5 wherein the gas density device further comprises a mounting plate positionable over the gas conduit and operably coupled to the connecting flange when coupled to the end cover.

8. The circuit breaker of claim 5 wherein the gas density device includes one of a gas sensing element cover or a pressure gauge coupled to the gas sensing element.

9. The circuit breaker of claim 5 further comprising a thermal insulating cover surrounding the gas density device and a solar cover positionable over the thermal insulating cover and mountable to the end cover.

10. A gas density monitoring kit for circuit breakers comprising
an end cap couplable to a circuit breaker tank, and
a gas density device couplable to the end cover and in fluid communication with an interior of the circuit breaker tank over a self sealing pathway through the end cover when the end cover is coupled to the circuit breaker tank and the gas density device is coupled to the end cover, wherein the self sealing pathway includes a self sealing valve mounted in the end cover,
wherein the gas density device comprises
a gas sensing element,
a gas conduit extending from the gas sensing element, and
a connecting flange coupled to the gas conduit, wherein when the gas density device is coupled to the end cover the connecting flange operably couples to and actuates the self sealing valve.

11. The circuit breaker of claim 10 wherein the self sealing pathway further comprises a gas port formed in the end cover at an angle to a longitudinal axis of the end cover.

12. The circuit breaker of claim 10 wherein the gas density device further comprises a mounting plate positionable over the gas conduit and operably coupled to the connecting flange when coupled to the end cover.

13. The circuit breaker of claim 10 wherein the gas density device includes one of a gas sensing element cover or a pressure gauge coupled to the gas sensing element.

14. The circuit breaker of claim 10 further comprising a thermal insulating cover surrounding the gas density device and a solar cover positionable over the thermal insulating cover and mountable to the end cover.

* * * * *